United States Patent
Aoyama et al.

(10) Patent No.: US 11,385,227 B2
(45) Date of Patent: Jul. 12, 2022

(54) MEMBRANE CARRIER AND KIT FOR TESTING LIQUID SAMPLE USING SAME

(71) Applicant: Denka Company Limited, Tokyo (JP)

(72) Inventors: Shuhei Aoyama, Tokyo (JP); Kenji Monden, Tokyo (JP)

(73) Assignee: Denka Company Limited, Tokyo (JP)

( * ) Notice: Subject to any disclaimer, the term of this patent is extended or adjusted under 35 U.S.C. 154(b) by 0 days.

(21) Appl. No.: 16/494,232

(22) PCT Filed: Mar. 28, 2018

(86) PCT No.: PCT/JP2018/012901
§ 371 (c)(1),
(2) Date: Sep. 13, 2019

(87) PCT Pub. No.: WO2018/181540
PCT Pub. Date: Oct. 4, 2018

(65) Prior Publication Data
US 2020/0132679 A1 Apr. 30, 2020

(30) Foreign Application Priority Data

Mar. 28, 2017 (JP) .............................. JP2017-062945
Mar. 28, 2017 (JP) .............................. JP2017-062946

(51) Int. Cl.
*G01N 33/544* (2006.01)
*G01N 21/78* (2006.01)
(52) U.S. Cl.
CPC .......... *G01N 33/544* (2013.01); *G01N 21/78* (2013.01)

(58) Field of Classification Search
CPC ..... G01N 33/544; G01N 21/78; G01N 33/558
See application file for complete search history.

(56) References Cited

U.S. PATENT DOCUMENTS

| 5,458,852 | A | 10/1995 | Buechler et al. |
| 7,824,611 | B2 * | 11/2010 | Buechler ............... G01N 33/558 435/287.1 |
| 9,347,931 | B2 | 5/2016 | Killard et al. |
| 2004/0077103 | A1 | 4/2004 | Buechler |
| 2009/0111197 | A1 | 4/2009 | Khan et al. |
| 2010/0255512 | A1 | 10/2010 | Wu et al. |
| 2011/0143450 | A1 | 6/2011 | White |

(Continued)

FOREIGN PATENT DOCUMENTS

| CN | 101180540 | 5/2008 |
| CN | 102171566 | 8/2011 |

(Continued)

OTHER PUBLICATIONS

Idegami Kotaro et al, translation of JP2013053897, Liquid Absorption Member and Vital Reaction Detecting System (Year: 2013).*

(Continued)

*Primary Examiner* — Jennifer Wecker
*Assistant Examiner* — Jonathan Bortoli
(74) *Attorney, Agent, or Firm* — Leydig, Voit & Mayer, Ltd.

(57) ABSTRACT

The present invention provides a membrane carrier 3 comprising a flow path 2 and a detection zone 3$y$, wherein a microstructure is provided at the bottom of the flow path 2 and a mean surface roughness of the microstructure is 0.005 to 10.0 μm.

9 Claims, 8 Drawing Sheets

(56) References Cited

U.S. PATENT DOCUMENTS

| | | | |
|---|---|---|---|
| 2011/0256551 A1* | 10/2011 | Linder | B01L 3/502746 435/7.1 |
| 2011/0284110 A1 | 11/2011 | Gagnon | |
| 2012/0107851 A1 | 5/2012 | Killard et al. | |
| 2012/0225496 A1 | 9/2012 | Yoshida | |
| 2016/0207042 A1* | 7/2016 | Dirckx | B01L 3/502784 |
| 2019/0329246 A1 | 10/2019 | Akiyama et al. | |

FOREIGN PATENT DOCUMENTS

| | | | | |
|---|---|---|---|---|
| CN | 102186643 | | 9/2011 | |
| CN | 102939160 | | 2/2013 | |
| EP | 1589063 | | 10/2005 | |
| JP | S63-014783 | | 4/1988 | |
| JP | H6-509424 | | 10/1994 | |
| JP | 2588174 | | 3/1997 | |
| JP | H10-123137 | | 5/1998 | |
| JP | 3513075 | | 3/2004 | |
| JP | 2005-077301 | | 3/2005 | |
| JP | 2007-024498 | | 2/2007 | |
| JP | 2009-241375 | | 10/2009 | |
| JP | 4597664 | | 12/2010 | |
| JP | 2012-002806 | | 1/2012 | |
| JP | 2012-505418 | | 3/2012 | |
| JP | 2012-524894 | | 10/2012 | |
| JP | 5147011 | | 2/2013 | |
| JP | 2013-053897 | | 3/2013 | |
| JP | 2013-113633 | | 6/2013 | |
| JP | 2013-148586 | | 8/2013 | |
| JP | 2014-062820 | | 4/2014 | |
| JP | 2014-081369 | | 5/2014 | |
| JP | 2014-098715 | | 5/2014 | |
| JP | 5609648 | | 10/2014 | |
| JP | 5799395 | | 10/2015 | |
| JP | 2016-011943 | | 1/2016 | |
| JP | 2016065253 | * | 4/2016 | C08J 9/40 |
| JP | 2017-040631 | | 2/2017 | |
| WO | WO 93/024231 | | 12/1993 | |
| WO | WO 2003/103835 | | 12/2003 | |
| WO | WO 2008/097360 | | 8/2008 | |
| WO | WO 2009/096529 | | 8/2009 | |
| WO | WO 2010/061598 | | 6/2010 | |
| WO | WO 2010/122158 | | 10/2010 | |
| WO | WO 2011/062157 | | 5/2011 | |
| WO | WO 2016/051974 | | 4/2016 | |
| WO | WO 2016/098740 | | 6/2016 | |
| WO | WO 2017/217406 | | 12/2017 | |
| WO | WO 2018/181549 | | 10/2018 | |

OTHER PUBLICATIONS

Chemical Entry Polymers: A Property Database 2019 Entry Name: Polydimethylsiloxane (Year: 2019).*

Young et al (see attached translation of JP2016065253) (Year: 2016).*

Kwak TJ, Nam YG, Najera MA, Lee SW, Strickler JR, Chang W-J (2016) Convex Grooves in Staggered Herringbone Mixer Improve Mixing Efficiency of Laminar Flow in MicroChannel. PLoS ONE 11(11): e0166068. doi:10.1371/journal. pone.0166068 (Year: 2016).*

Polyurethane Y-304 | C17H16N2O4—PubChem (Year: 2021).*

Extended European Search Report, dated Apr. 20, 2020, corresponding to European Patent Application No. 18776540.9, 12 pp.

U.S. Appl. No. 16/309,877, dated Dec. 13, 2018.

U.S. Appl. No. 16/494,183, dated Sep. 13, 2019.

Partial Supplementary European Search Report, dated Feb. 19, 2020, for corresponding European Application No. 18776540.9, 13 pp.

International Preliminary Report on Patentability, dated Dec. 27, 2018, corresponding to International Application No. PCT/JP2017/021801 (filed Jun. 13, 2017), 16 pp.

International Preliminary Report on Patentability, dated Oct. 10, 2019, corresponding to International Application No. PCT/JP2018/012926 (filed Mar. 28, 2018), 8 pp.

International Preliminary Report on Patentability, dated Oct. 10, 2019, corresponding to International Application No. PCT/JP2018/012901 (filed Mar. 28, 2018), 9 pp.

Rivas, Lourdes (2014) "Improving Sensitivity of Gold Nanoparticle-Based Lateral Flow Assays by Using Wax-Printed Pillars as Delay Barriers of Microfluidics," Lab on a Chip, 14:4406-4414.

Search Report and Written Opinion, dated Jul. 18, 2017, corresponding to International Application No. PCT/JP2017/021801 (filed Jun. 13, 2017), 16 pp.

Search Report and Written Opinion, dated Jun. 26, 2018, corresponding to International Application No. PCT/JP2018/012926 (filed Mar. 28, 2018), 8 pp.

Search Report and Written Opinion with English translation, dated Jun. 26, 2018, corresponding to International Application No. PCT/JP2018/012901 (filed Mar. 28, 2018), parent of the present application, 2 pp.

Office Action and Search Report, dated Apr. 25, 2022, corresponding to Chinese Patent Application No. 201880012129, relevance found on pp. 6-7.

* cited by examiner (a)

(b)

(a)

(b)

(a)

(b)

MEMBRANE CARRIER AND KIT FOR TESTING LIQUID SAMPLE USING SAME

CROSS-REFERENCE TO RELATED APPLICATIONS

This application is a U.S. National Stage Application filed under 35 U.S.C. § 371 of International Application No. PCT/JP2018/012901, filed Mar. 28, 2018, which claims the benefit of Japanese Application No. JP 2017-062945, filed Mar. 28, 2017 and Japanese Application No. JP 2017-062946, filed Mar. 28, 2017. All three of these applications are hereby incorporated by reference in their entireties.

TECHNICAL FIELD

The present invention relates to a membrane carrier and a liquid sample test kit using the carrier.

BACKGROUND ART

Recently, Point of Care Testing (POCT) reagents using, for example, antigen-antibody reactions for determining contraction of infectious diseases, pregnancy, blood sugar level and the like, have attracted attention. The POCT reagents, which are test reagents used near subjects or directly used by the subjects, have such characteristics as capability of determination of test results in a short time, simple operation and low cost. By virtue of these characteristics, the POCT reagents are frequently used in, for example, medical examinations at the stage of mild symptoms and regular medical examinations and used as an important examination tool in home medical care which is expected to expand from now on.

In most POCT reagents, determination is made by introducing a liquid sample such as blood in a test kit and detecting a predetermined target substance contained in the liquid sample. As a method for detecting a predetermined target substance from a liquid sample, immunochromatography is frequently used. The immunochromatography is a technique for detecting a substance by delivering a liquid drop onto a membrane carrier of a test kit, allowing the liquid drop to move on the membrane carrier, allowing a target substance to bind to a label substance and the resultant to further bind specifically to a substance (hereinafter referred to as a detection substance) immobilized in the test kit to produce a color or mass change, and detecting the change. The detection substance may be called also as a reagent.

As a membrane carrier on which a liquid sample is allowed to move, a nitrocellulose membrane is often used (Patent Literature 1). The nitrocellulose membrane has many micropores having a diameter of about several μm and a liquid sample moves through the micropores with the help of capillary force.

However, the nitrocellulose membrane, which is derived from a natural product, has pores not uniform in size and arrangement. Because of this, the flow rate of a liquid sample varies depending on the membranes. If the flow rate varies, the time taken for detecting a target substance varies, with the result that a wrong determination: "binding was not detected" may be made before the target substance binds.

In order to overcome the above problem, a liquid sample test kit in which a micro flow-path is artificially produced, is devised (Patent Literature 2). In Patent Literature 2, a membrane carrier having a uniform structure can be prepared by use of a synthetic material, with the result that the possibility of wrong determination: "binding was not detected" made before the target substance binds, can be reduced.

When a synthetic material is used, it is necessary to increase affinity of a detection substance with the material in order to improve detection sensitivity. Thus, it is considered to be effective that various surface treatments are applied to the material, in advance (Patent Literatures 3 and 4). Patent Literature 5 discloses a membrane carrier for a liquid sample test kit for detecting a target substance in a liquid sample, having at least one flow-path transporting the liquid sample in which a microstructure producing capillary action for transporting the liquid sample is formed at the bottom of the flow path.

CITATION LIST

Patent Literature

Patent Literature 1: Japanese Unexamined Patent Publication No. 2014-062820
Patent Literature 2: Japanese Patent No. 5799395
Patent Literature 3: Japanese Unexamined Patent Publication No. 2013-113633
Patent Literature 4: U.S. Patent Application Publication No. 2011/0284110
Patent Literature 5: WO 2016/098740

SUMMARY OF INVENTION

Technical Problem

In Patent Literatures 3 and 4, neither the effect of surface treatment on a material nor proper treatment conditions for improving sensitivity were provided. As a result, the performance of a system was not sufficiently provided. In Patent Literatures 3 to 5, neither the mean surface roughness of the microstructure of a membrane carrier nor the ratio of number of oxygen atoms of a surface of a detection zone (number of oxygen atoms/(number of carbon atoms+number of nitrogen atoms+number of oxygen atoms)) is described.

The present invention provides a membrane carrier enabling highly sensitive determination.

Solution to Problem

More specifically, the present invention is as follows:
(1) A membrane carrier comprising a flow path and a detection zone, in which a microstructure is provided at the bottom of the flow path and a mean surface roughness in the microstructure is 0.005 to 10.0 μm.
(2) A membrane carrier comprising a flow path and a detection zone, in which a microstructure is provided at the bottom of the flow path; at least one of a carbon atom and a nitrogen atom and an oxygen atom are present on a surface of the detection zone; and a ratio of the number of oxygen atoms relative to a total number of individual types of atoms (number of oxygen atoms/(number of carbon atoms+number of nitrogen atoms+number of oxygen atoms)) is 0.01 to 0.50.
(3) The membrane carrier according to (1) or (2), in which a height of the microstructure is 5 to 1000 μm.
(4) The membrane carrier according to any one of (1) to (3), in which a bottom diameter of the microstructure is 5 to 1000 μm.
(5) The membrane carrier according to any one of (1) to (4), in which a nearest distance between the microstructures within the flow path is 0 to 500 μm.

(6) The membrane carrier according to any one of (1) to (5), in which an aspect ratio of the microstructure is 0.1 to 10.

(7) The membrane carrier according to any one of (1) to (6), being a membrane carrier for a test kit, which detects a target substance in a liquid sample.

(8) The membrane carrier according to (7), in which the detection zone produces a color change when a target substance is detected.

(9) The membrane carrier according to (7) or (8), in which a detection substance responsible for producing a color change when a target substance is detected is immobilized in the detection zone.

(10) A liquid sample test kit having the membrane carrier according to any one of (1) to (9).

Advantageous Effects of Invention

The present invention can provide a membrane carrier enabling highly sensitive determination.

DESCRIPTION OF EMBODIMENTS

Embodiments of the present invention will be described below. The embodiments of the present invention are not limited to Examples (later described) and may be modified in various ways within the range of a technical idea thereof.

The membrane carrier according to an embodiment is a membrane carrier for a liquid sample test kit, which detects a target substance in a liquid sample.

The target substance herein, which is not limited, may be any substance as long as it can undergo an antigen-antibody reaction with various pathogens, various clinical markers and antibodies. Examples of the target substance include, but are not particularly limited to, antigens of viruses such as influenza virus, norovirus, adenovirus, RS virus, HAV, HBs and HIV; antigens of bacteria such as MRSA, Group-A *streptococcus*, Group-B *streptococcus* and *Legionella* bacteria; toxins produced by bacteria, *Mycoplasma*, *Chlamydia trachomatis*, hormones such as human chorionic gonadotropin; and C reactive protein, myoglobin, myocardial troponin, various tumor markers, agrochemicals and environmental hormones. If the target substance is particularly a substance that must be quickly detected and treated, such as influenza virus, norovirus, C reactive protein, myoglobin and myocardial troponin, the membrane carrier for a liquid sample test kit is extremely useful. The target substance may be an antigen, which solely induces an immune response, or may be a hapten, which cannot induce an immune response by itself but can bind to an antibody through an antigen-antibody reaction. The target substance is usually suspended or dissolved in a liquid sample. The liquid sample may be a sample obtained by suspending or dissolving the target substance in, for example, a buffer solution.

Figure 1:
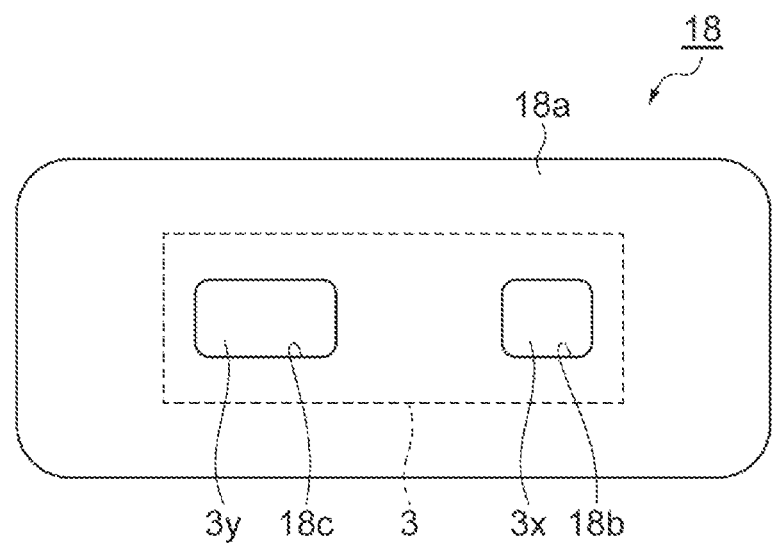
FIG. 1 shows a schematic top view of a test kit which is an embodiment of the present invention.

The liquid sample test kit according to the embodiment (hereinafter referred to also simply as the "test kit") detects a target substance in a liquid sample. FIG. 1 is a schematic top view of a test kit. For example, as shown in FIG. 1, a test kit 18 has a membrane carrier 3 and a case 18a for accommodating the membrane carrier 3. The membrane carrier 3 has, in the surface thereof, a drop zone 3x on which a drop of a liquid sample is delivered and a detection zone 3y for detecting a target substance in a liquid sample. The drop zone 3x is exposed in a first opening 18b of the case 18a. The detection zone 3y is exposed in the second opening 18c of the case 18a.

Figure 2:
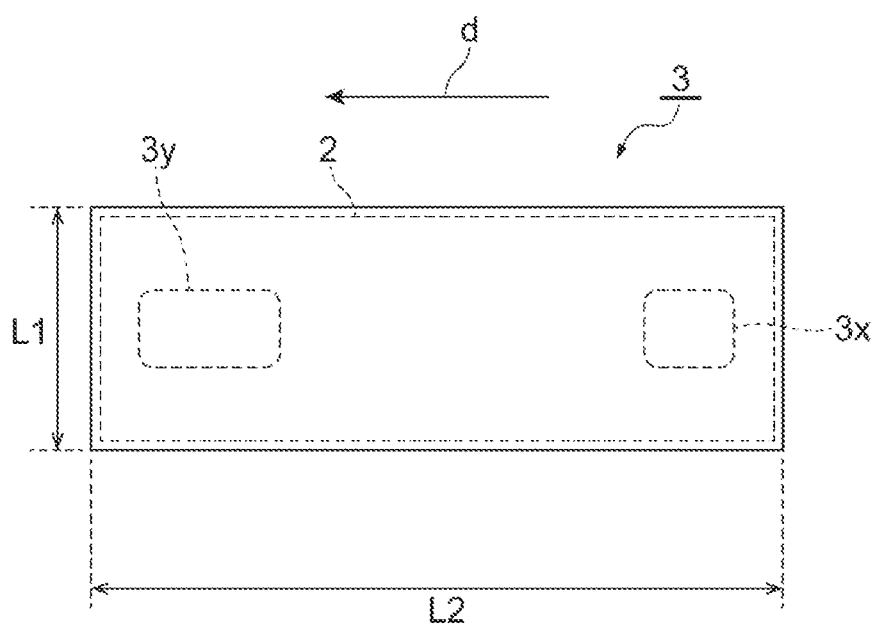
FIG. 2 shows a schematic top view of a membrane carrier which is an embodiment of the present invention.

FIG. 2 is a schematic top view of the membrane carrier 3. As shown in FIG. 2, the membrane carrier 3 has at least one flow path 2 for transporting a liquid sample. At the bottom of the flow path 2, a microstructure is provided (not shown, details will be described later). The microstructure is present at least between the drop zone 3x and the detection zone 3y. The microstructure may be provided over the entire surface of the membrane carrier 3. The entire surface of the membrane carrier 3 may serve as the flow path 2 for a liquid sample. Owing to the microstructure, capillary action is produced. A liquid sample is transported from the drop zone 3x to the detection zone 3y (along transport direction d) through the microstructure with the help of the capillary action produced by the microstructure. When a target substance in a liquid sample is detected in the detection zone 3y, the color of the detection zone 3y changes.

The entire shape of the membrane carrier 3 is not particularly limited; however, the shape may be, for example, a polygon such as a rectangle, a circle or an ellipsoid. If the membrane carrier 3 is a rectangle, the length (length of the shorter side) L1 of the membrane carrier 3 may be, for example, 2 mm to 100 mm and the width (length of the longer side) L2 of the membrane carrier 3 may be, for example, 2 mm to 100 mm. The thickness of the membrane carrier excluding the heights of the microstructure, may be, for example, 0.1 mm to 10 mm.

FIGS. 3 to 6 each show a microstructure provided at the bottom of the flow path according to the embodiment and an example of convex portions constituting the microstructure. In each of FIGS. 3 to 6, (a) is a plan view (top view) of microstructure; and (b) is a perspective view of one of the convex portions constituting the microstructure. As shown in FIGS. 3 to 6, a microstructure 7 is an assembly of convex portions 8. More specifically, the membrane carrier 3 has a flat part 9 corresponding to the bottom of the flow path 2 of a liquid sample and a plurality of convex portions 8 corresponding to the flat part 9. The space between the convex portions 8 serves as flow path 2 for transporting a liquid sample along the surface of the membrane carrier 3 with the help of capillary action. In other words, space in the microstructure 7 serves as the flow path 2 for transporting a liquid sample along the surface of the membrane carrier 3 by capillary action. The convex portions 8 may be arranged on the surface of the membrane carrier 3 in a regular manner or a translational symmetric manner.

Figure 3:
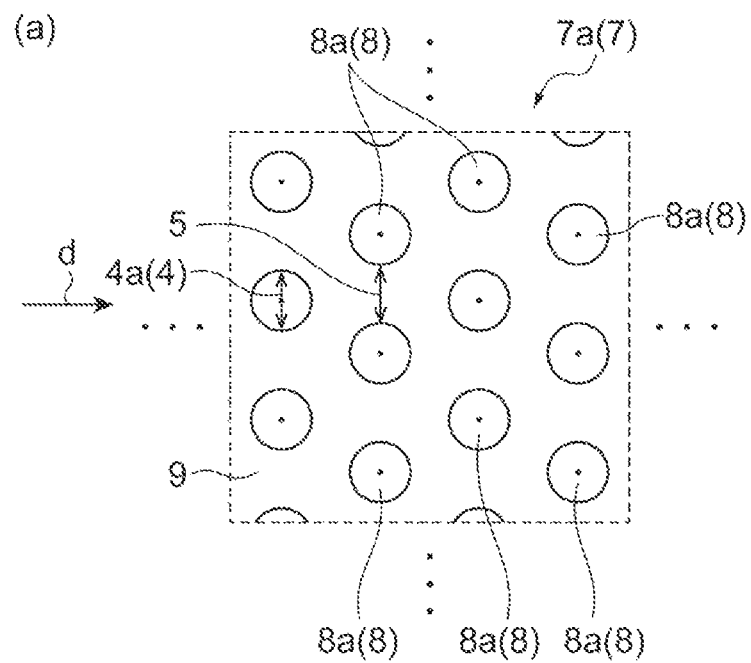
FIG. 3 shows (a) a plan view (top view) of microstructures which is an embodiment of the present invention; and (b) a perspective view of a convex portion constituting the microstructure shown in (a).
Figure 3:
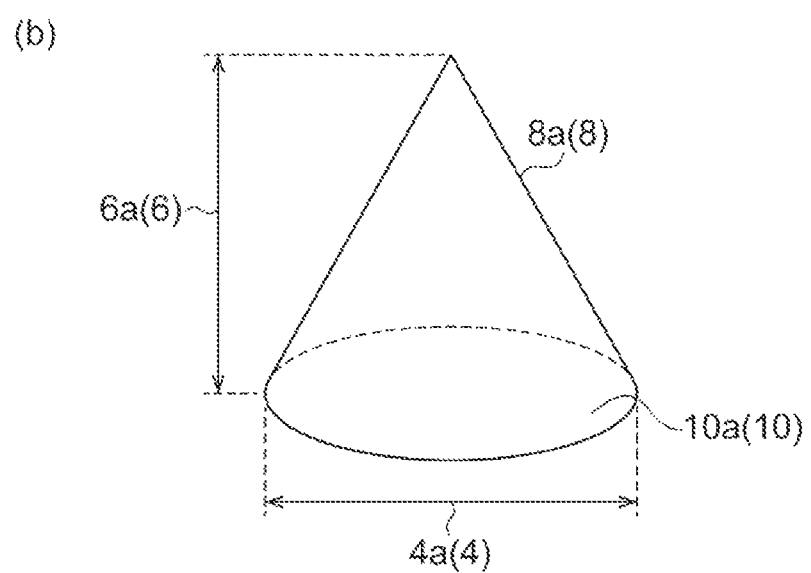
Figure 4:
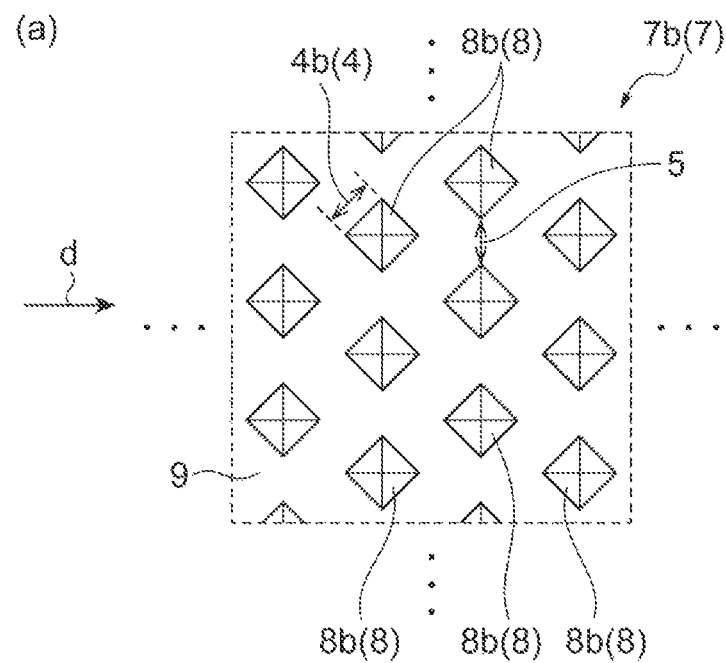
FIG. 4 shows (a) a plan view (top view) of a microstructure which is an embodiment of the present invention; and (b) a perspective view of a convex portion constituting the microstructure shown in (a).
Figure 4:
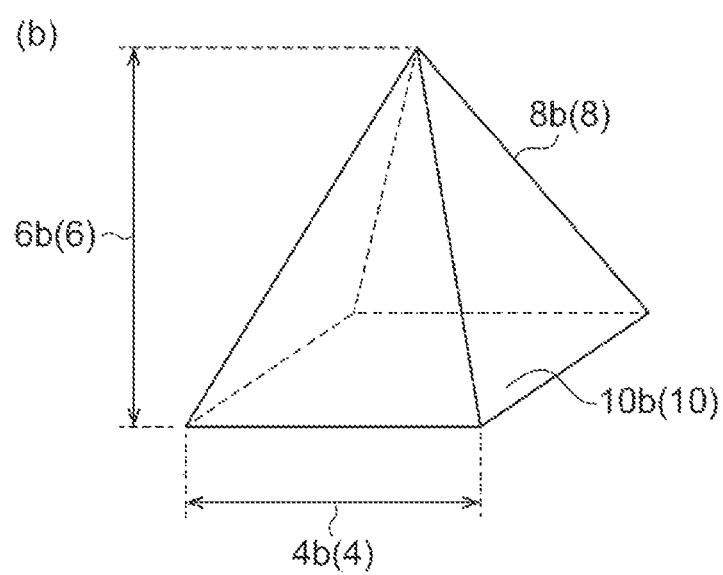
Figure 5:
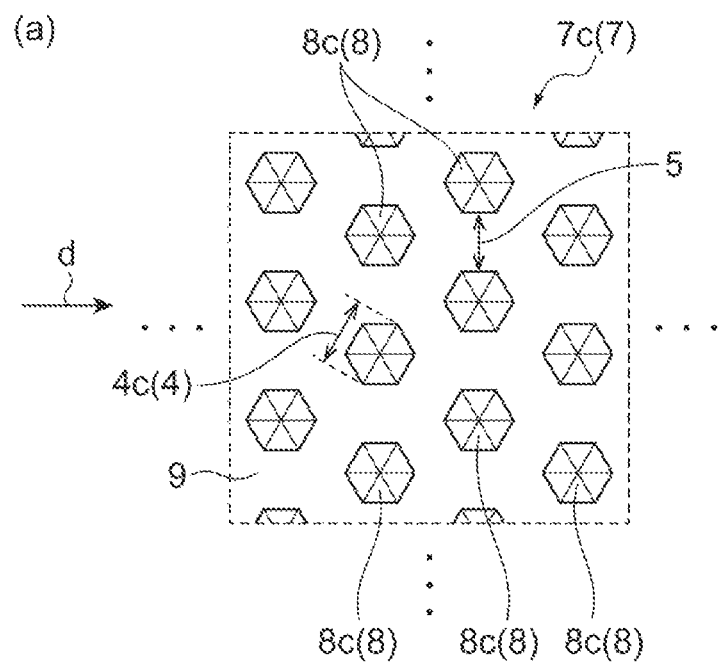
FIG. 5 shows (a) a plan view (top view) of a microstructure which is an embodiment of the present invention; and a perspective view of a convex portion constituting the microstructure shown in (a).
Figure 5:
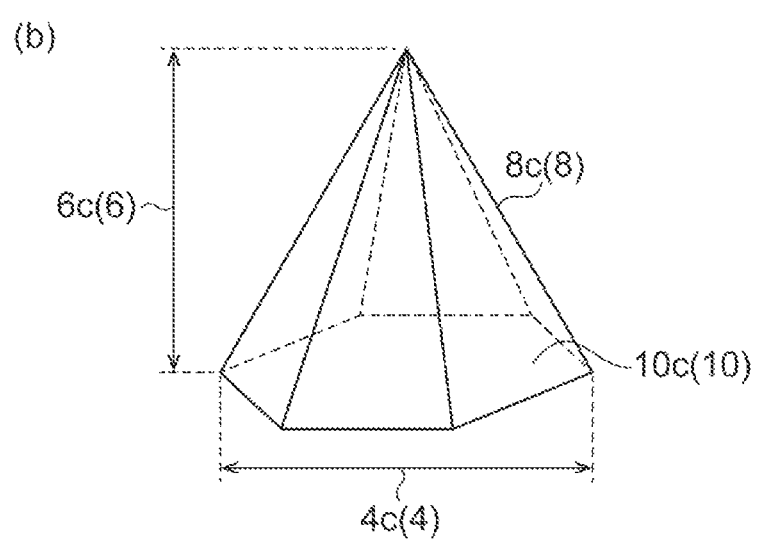
Figure 6:
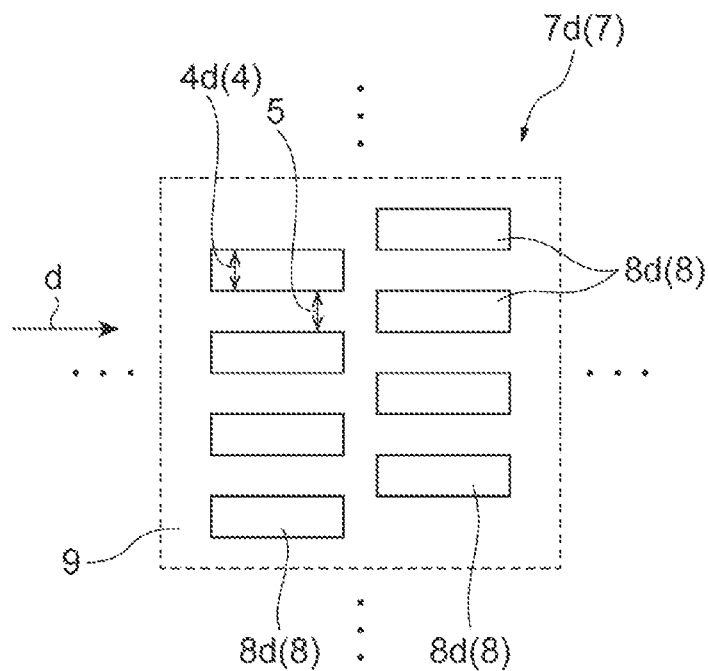
FIG. 6 shows (a) a plan view (top view) of a microstructure which is an embodiment of the present invention; and (b) a perspective view of a convex portion constituting the microstructure shown in (a).
Figure 6:
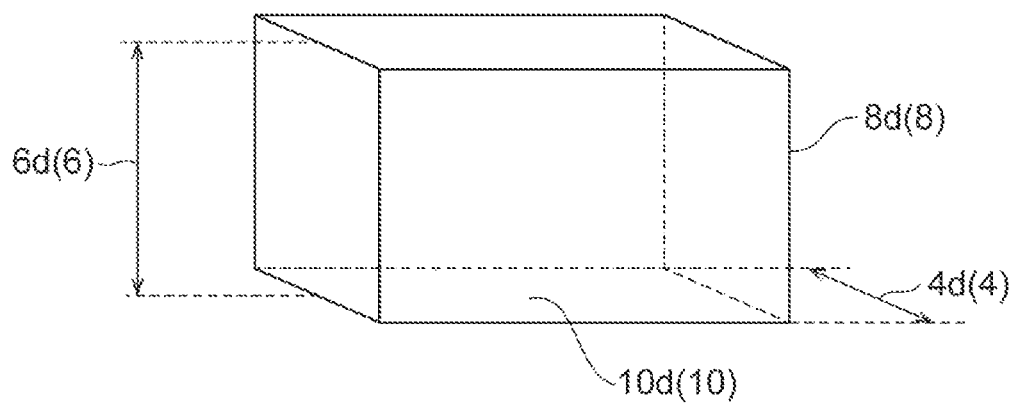

The shape of convex portions 8 constituting the microstructure 7 can be freely selected. Examples of the shape of the convex portions 8 include a cone, a polygonal pyramid, a truncated cone, a truncated polygonal pyramid, a cylinder, a polygonal column, a hemisphere and a semi-ellipsoid. As the shape of the bottom of a microstructure, for example, a circle or polygon (for example, square, rhombus, rectangle, triangle or hexagon) is mentioned. For example, the shape of the convex portions 8a may be a cone as shown in FIG. 3. For example, the shape of the convex portions 8b may be a square pyramid as shown in FIG. 4. For example, the shape of the convex portions 8c may be a hexagonal pyramid as shown in FIG. 5. For example, as shown in FIG. 6, the shape of the convex portion 8d may be a quadrangular prism (line-space structure where a convex portion 8d is linear). For the reasons that when the microstructure 7 is looked down (seen from the top) the entire surface of the membrane carrier 3 can be seen and a color change when a target substance is detected can be easily checked by an optical means, a cone structure such as a cone and polygonal pyramid is suitable as the shape of the convex portions 8, among the aforementioned shapes. Of cone structures, a circular cone is preferable.

The shape of the convex portions 8 constituting the microstructure 7 is not necessary to be a geometrically accurate shape and may be a shape having a round corner and a shape having micro-convexoconcaves in the surface.

The diameter 4 of each of the bottom surfaces 10 of the convex portions 8 constituting the microstructure 7 is preferably 5 µm or more and 1000 µm or less, and more preferably, 10 µm or more and 500 µm or less. If the diameter 4 of each of the bottom surfaces 10 of the convex portions 8 is 5 µm or more, the accuracy of microfabrication can be kept low and cost for forming the microstructure 7 tends to reduce. If the diameter 4 of each of the bottom surfaces 10 of the convex portions 8 is 1000 µm or less, the number of convex portions 8 in a single test kit increases and a liquid sample can be easily developed.

The diameter 4 of each of the bottom surfaces 10 of the convex portions 8 is defined as the representative length of the bottom surface 10 of the convex portion 8. The representative length defining the bottom surface 10 is a diameter if the shape of the bottom surface 10 is a circle; the length of the shortest side if the shape is a triangle or a rectangle; the length of the longest diagonal line if the shape is a polygon of a pentagon or more; and a maximum length of the bottom surface 10 in the case of shapes except the aforementioned ones.

As shown in FIG. 3, if the shape of the convex portion 8a is a cone, the diameter 4a of the bottom surface 10a of the convex portion 8a corresponds to the diameter of the bottom (circle) of the cone. As shown in FIG. 4, if the shape of the convex portion 8b is a regular square pyramid, the diameter 4b of the bottom surface 10b of the convex portion 8b is the length of sides of the bottom surface (regular square) 10b. As shown in FIG. 5, if the shape of the convex portion 8c is a regular hexagonal pyramid, the diameter 4c of the bottom surface 10c of the convex portion 8c is the length of a diagonal line (length of the longest diagonal line) passing through the center of the bottom surface (regular hexagon) 10c. As shown in FIG. 6, if the shape of the convex portion 8d is a rectangle, the diameter 4d of the bottom surface 10d of the convex portion 8d is the length of the shortest side of the bottom surface (rectangle) 10d (in FIG. 6, the length of the side perpendicular to the transport direction d of a liquid sample).

The height 6 of each of the convex portions 8 constituting the microstructure 7 is preferably 5 µm to 1000 µm and more preferably 10 µm to 500 µm. If the height 6 of the convex portions 8 is 5 µm or more, the volume of the flow path 2 increases, with the result that a liquid sample can be developed in a shorter time. If the height 6 of each of the convex portions 8 is 1000 µm or less, time and cost for forming the microstructure 7 can be reduced, with the result that it becomes easy to prepare the microstructure 7.

The height 6 of the convex portion 8 is defined as a maximum length of the convex portion 8 in the direction perpendicular to the flat part 9. As shown in FIG. 3, if the shape of the convex portion 8a is a cone, the height 6a of the convex portion 8a is a maximum length (the height of the cone) of the convex portion 8a in the direction perpendicular to the flat part 9. As shown in FIG. 4, if the shape of the convex portion 8b is a square pyramid, the height 6b of the convex portion 8b is a maximum length (the height of the square pyramid) of the convex portion 8b in the direction perpendicular to the flat part 9. As shown in FIG. 5, if the shape of the convex portion 8c is a hexagonal pyramid, the height 6c of the convex portion 8c is a maximum length (the height of the hexagonal pyramid) of the convex portion 8c in the direction perpendicular to the flat part 9. As shown in FIG. 6, if the shape of the convex portion 8d is a quadrangular prism, the height 6d of the convex portion 8d is a maximum length (the height of the quadrangular prism) of the convex portion 8d in the direction perpendicular to the flat part 9.

The nearest distance 5 between the convex portions 8 constituting the microstructure 7 is preferably 0 to 500 µm. It is preferably 500 µm or less and more preferably 2 µm or more and 100 µm or less. It is not conceivable that the nearest distance 5 between the convex portions 8 is less than 0 µm. If the nearest distance is 500 µm or less, the contact area between a liquid sample and the flow path 2 increases and thereby capillary force increases, with the result that a liquid sample can be more easily moved. The "nearest distance between the convex portions 8" herein refers to the nearest distance between a pair of adjacent convex portions 8.

The aspect ratio of each of the convex portions 8 constituting the microstructure 7 is preferably 0.1 to 10 and more preferably 0.1 to 2.0. The aspect ratio herein refers to a value obtained by dividing the height 6 (Lh) of the convex portion 8 by the representative length (diameter 4) (Lv) of the bottom surface 10 of the convex portion 8, (Lh/Lv). If the aspect ratio is 0.1 or more, the contact area between of a liquid sample and the flow path 2 increases and thereby capillary force increases, with the result that a liquid sample is more easily moved. If the aspect ratio is 10 or less, it becomes easy to prepare the microstructure.

The microstructure 7 and the membrane carrier 3 of the liquid sample test kit 18 of the embodiment may be made of a thermoplastic. In other words, the membrane carrier 3 having the microstructure 7 can be produced by processing a film-like base material made of a thermoplastic.

Examples of the processing method include thermal imprint, UV imprint, injection molding, etching, photolithography, machine cutting and laser processing. Of them, thermal imprint to a thermoplastic is suitable as a method for applying a precise processing at low cost. Examples of the thermoplastic include a polyester resin, a polyolefin resin, a polystyrene resin, a polycarbonate resin, a fluororesin and an acrylic resin. More specifically, various types of resins including polyethylene terephthalate (PET), a cycloolefin polymer (COP), polypropylene (PP), polystyrene (PS), polycarbonate (PC), polyvinylidene fluoride (PVDF), polymethylmethacrylate (PMMA) and polyethylene (PE), can be used.

In the case of processing using a mold, such as imprint and injection molding, since the top of a cone is narrow compared to the bottom, the volume of metal scraped out in forming the mold is smaller than a columnar mold having the same bottom area, and thus, the mold can be prepared at low cost with a cone. In this case, a target substance in a liquid sample can be detected at low cost.

As described above, the membrane carrier 3 has the microstructure 7 provided over the surface of the membrane carrier 3, a flow path 2 formed of the microstructure 7 for transporting a liquid sample and a detection zone (detection section) 3y for detecting a target substance in a liquid sample. The membrane carrier 3 may be a membrane carrier 3 for a liquid sample test kit 18, which detects a target substance in a liquid sample.

In an embodiment, the mean surface roughness (Ra) of the membrane carrier 3 in the microstructure 7 is 0.005 to 10.0 μm. The mean surface roughness of the membrane carrier 3 in the microstructure 7 is preferably 0.1 μm or more, more preferably 0.2 μm or more, further preferably 0.5 μm or more and further more preferably 1 μm or more. The mean surface roughness of the membrane carrier 3 may be 10 μm or less, 5 μm or less, 1 μm or less or 0.1 μm or less. The mean surface roughness (Ra) of the membrane carrier 3 in the microstructure 7 refers to a mean surface roughness of the convex portions 8 and the definition determined in JIS B0601: 2013 is employed. The mean surface roughness of the membrane carrier 3 in microstructure 7 can be rephrased as a mean surface roughness of convex portions 8 in the microstructure 7 of the membrane carrier 3.

In the membrane carrier 3, the mean surface roughness (Ra) of the flat part 9 may be 0.005 to 10.0 μm. The mean surface roughness of the flat part 9 may be a value indicated as an average roughness of the above membrane carrier. The mean surface roughness (Ra) of the flat part 9 is preferably 10 μm or less, more preferably 5 μm or less, further preferably 3 μm or less and further more preferably 2 μm or less.

Figure 7:
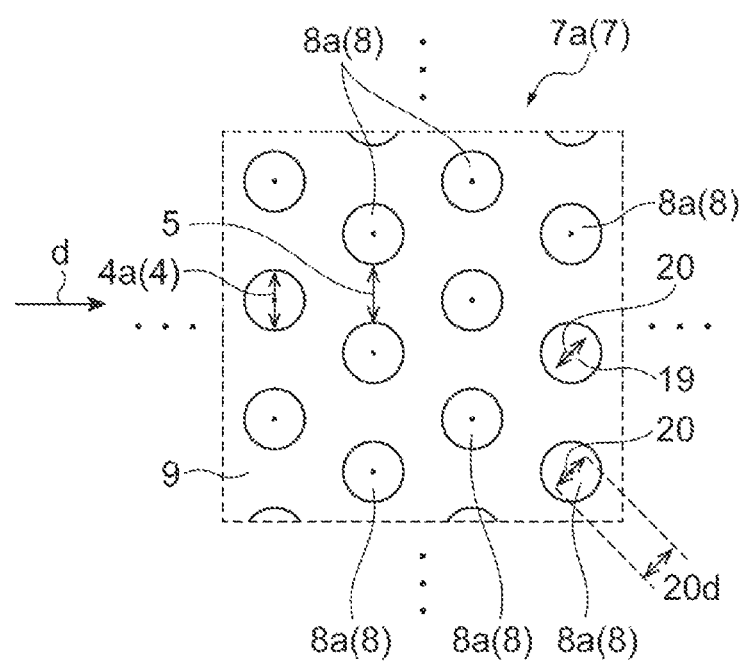
FIG. 7 shows a schematic top view of a microstructure which is an embodiment of the present invention.

FIG. 7 is used for describing a method for determining a mean surface roughness of convex portions 8 of the microstructure 7. Roughness (profile) is measured along the surface of the convex portion 8 (along the linear line 20 in the top view) as a midpoint at a vertex center (for example, convex center 19) of the convex portion 8. The linear line 20 is any line passing through the vertex center (for example, convex center 19) as a midpoint and having a length of 20d. The length 20d is the same length as the diameter of the bottom of the convex portion 8. If the linear line 20 is a straight line placed on the same plane (for example, both ends and the center are present on the same plane), more specifically, the convex portion 8 has a shape such as a truncated cone, a truncated polygonal pyramid, a cylinder and a polygonal column, a mean surface roughness (Ra) defined in JIS B0601 is calculated from the roughness profile. If the linear line 20 is a straight line not on the same plane, more specifically, the convex portion 8 has a shape such as a cone, a polygonal pyramid, a hemisphere or a semi-ellipsoid, tilt correction is provided based on the roughness profile and a mean surface roughness (Ra) defined in JIS B0601 is calculated as a flat plane.

If the membrane carrier 3 having the microstructure 7 is produced by thermal imprint, the mean surface roughness of the membrane carrier 3 in the microstructure 7 can be adjusted to fall the aforementioned numerical range by, for example, etching, photolithography, machine cutting and laser processing. Particularly, the mean surface roughness of the membrane carrier 3 in the microstructure 7 is preferably adjusted by controlling a mean surface roughness of the mold to be used in thermal imprint, to be a predetermined value. For example, the mean surface roughness of the membrane carrier 3 in the microstructure 7 is preferably adjusted by processing the surface of a mold by, for example, etching, photolithography, machine cutting, polishing and/or laser processing. As the polishing, cutting by, for example, dicing and sand blast, can be mentioned. In the case of the laser processing, a mean surface roughness can be adjusted by controlling output of a laser.

More specifically, it is preferable that the method for producing a test kit 18 according to the embodiment has a step of producing a membrane carrier 3 having a microstructure 7 by thermal imprint (thermal imprint step). In the thermal imprint step, a mold having a plurality of concave portions in the surface is applied to a film-like substrate formed of, for example, a thermoplastic so as to face the surface to the substrate, and the substrate is heated. In this manner, a membrane carrier 3 having a microstructure 7 having a plurality of convex portions 8, which correspond to the shapes of the concave portions, and a flat part 9, is formed.

In an embodiment, in the surface of the detection zone, at least one of a carbon atom and a nitrogen atom, and an oxygen atom are present.

The ratio of number of oxygen atoms to a total number of individual types of atoms (number of oxygen atoms/(number of carbon atoms+number of nitrogen atoms number of oxygen atoms)) is 0.01 to 0.50. In the membrane carrier of an embodiment, the ratio of number of oxygen atoms (number of oxygen atoms/(number of carbon atoms+number of nitrogen atoms f number of oxygen atoms)) in the surface of the detection zone is 0.01 or more, preferably 0.05 or more, more preferably 0.10 or more and further preferably 0.20 or more. In the membrane carrier of an embodiment, the ratio of number of oxygen atoms (number of oxygen atoms/(number of carbon atoms number of nitrogen atoms+number of oxygen atoms)) in the surface of the detection zone is 0.50 or less, preferably 0.40 or less, more preferably 0.38 or less, further preferably 0.36 or less, further more preferably 0.30 or less and still further more preferably, 0.10 or less. As the ratio of number of oxygen atoms in the surface of the detection zone increases, a detection substance is more easily immobilized to the surface. If the detection substance is immobilized to the surface, the amount of the detection substance flowing out when a liquid sample is developed, is reduced and highly sensitive detection can he made. If the ratio of number of oxygen atoms in the surface of the detection zone is 0.50 or less, occurrence of a wrong detection caused by reacting a label and a detection substance when a solution containing no target substance is developed is further reduced.

The ratio of number of oxygen atoms in the surface of the detection zone is calculated based on an X ray electron spectroscopy (XPS). Calculation of the ratio of number of oxygen atoms based on XPS will be described below. The spectrum obtained by measurement is subjected to correction of binding energy performed by a C—C bond in a C1s spectrum. In the spectrum obtained after the binding energy correction, for each of the peaks in the C1s spectrum, N1s spectrum and O1s spectrum, background (BG) is subtracted. Each of the peak areas (signal intensity) of individual atoms calculated by subtracting BG from the respective peaks is divided by a correction coefficient (relative sensitivity coefficient, transparent function and kinetic energy correction) and calculation is made such that the total of the areas after correction becomes 100. Individual values thus obtained are regarded as the number of carbon atoms, number of nitrogen atoms and number of oxygen atoms, and the ratio of number of oxygen atoms (number of oxygen atoms/(number of carbon atoms+number of nitrogen atoms+number of oxygen atoms)) is calculated.

The ratio of number of oxygen atoms in the surface of the detection zone can be adjusted so as to fall within the aforementioned range by treating the surface of the detection zone. Examples of the surface treatment method include, but are not limited to, plasma processing, corona treatment, UV irradiation, UV/ozone treatment, surface modification with, for example, 3-aminopropyltriethoxysilane and glutaraldehyde.

A surface treatment is preferably applied only to the detection zone. If the surface treatment is applied only to the detection zone, a detection substance is not immobilized to the non-detection zone (region except the detection zone) in the flow path and the detection substance can be highly efficiently immobilized only to the detection zone. As a result, it becomes easy to recognize a detection signal in the detection zone (S/N ratio increases).

Figure 8:
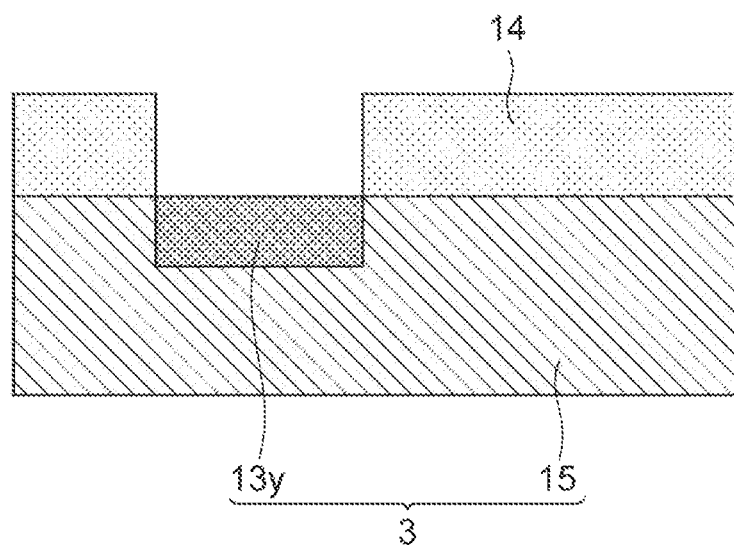
FIG. 8 shows a schematic view for explaining a surface treatment according to an embodiment of the present invention.

As a method for reforming the surface of the detection zone by selectively treating the surface of the detection zone, a method of applying a mask (shield) to the region except the detection zone and applying a surface treatment to the detection zone exposed. FIG. 8 is for use in explaining a method of selectively applying a surface treatment to the surface of the detection zone. A shield 14 having an opening is arranged on the membrane carrier 3 to expose the detection zone (a surface treated section). The portion of the membrane carrier 3 covered with the shield 14 becomes an untreated portion (non-detection zone) 15. As the shield 14, a metal plate is preferable. A surface treatment is applied to the exposed portion to obtain a membrane carrier 3 having the ratio of number of oxygen atoms in the surface of the detection zone within the above range.

In the above embodiment, as a material for a membrane carrier, a resin having a surface ratio of number of oxygen atoms (number of oxygen atoms/(number of carbon atoms+number of nitrogen atoms+number of oxygen atoms)) of less than 0.01 is preferably used and a resin having a surface ratio of number of oxygen atoms of 0.005 or less is more preferably used. A resin having a surface ratio of number of oxygen atoms of less than 0.01 is a resin containing no oxygen atom in a structural formula of a main component and may be a resin containing a carbon atom, neither a nitrogen atom nor an oxygen atom, such as a polyolefin resin, a polystyrene resin and a fluororesin. Examples of the resin include polyethylene (PE), a cycloolefin polymer (COP), polypropylene (PP), polystyrene (PS) and polyvinylidene fluoride (PVDF). A resin having a surface ratio of number of oxygen atoms of less than 0.01 may be a resin containing a carbon atom and nitrogen atom and not containing an oxygen atom, such as a polyimide resin. If a resin containing a carbon atom, neither a nitrogen atom nor oxygen atom is used, the ratio of number of oxygen atoms (number of oxygen atoms/(number of carbon atoms+number of nitrogen atoms+number of oxygen atoms)) of the detection zone becomes substantially equal to the number of oxygen atoms/(number of carbon atoms+number of oxygen atoms).

When a surface ratio of number of oxygen atoms is 0.005 or less, if a membrane carrier is formed, a test kit is produced by using the membrane carrier, and a liquid sample is developed, the adhesion of a label in the non-detection zone is further suppressed. When a label is attached to a non-detection zone, even if a signal having the same intensity is generated in the detection zone, the signal is rarely recognized (S/N ratio decreases).

In a liquid sample test kit 18 according to the embodiment when a target substance is detected in detection zone 3y of the membrane carrier 3, color changes. The color change may be a color change observable by an optical means.

As the optical means, two methods: a visual determination means and means of measuring a fluorescence intensity, are mostly mentioned. In the case of visual determination, it is preferable to produce a color change expressed by a color difference ($\Delta E$ described in JIS Z8781-4:2013) of 0.5 or more between two color stimuli before and after detection when the color is measured by the color system of CIE1976L*a*b* color space. If the color difference is 0.5 or more, visually determination of color difference can be easily made. In the case of determination based on fluorescence-intensity measurement, it is preferable to produce a color difference satisfying a ratio of the fluorescence intensity (Fl1) in the detection zone 3y to the fluorescence intensity (Fl2) in upstream region and downstream region adjacent to the detection zone 3y, (Fl1/Fl2)=10/1 or more. If the ratio is 10/1 or more, signal and noise can be easily separated.

To prepare the detection zone 3y in the liquid sample test kit 18 of the embodiment, a detection substance is immobilized in at least part of the flow path 2, in an embodiment. More specifically, a detection substance detecting a target substance is immobilized in the detection zone 3y color change in the detection zone 3y is produced by holding a target substance by the detection substance (through reaction with the detection substance) in the detection zone 3y.

In other words, a method for producing the liquid sample test kit 18 comprises a step of immobilizing, to the detection zone 3y, a detection substance which produces a color change by holding the target substance in the detection zone 3y. For the reason that a detection substance (reagent) can be efficiently immobilized in the detection zone 3y, the surface treatment may be previously applied to the site of the membrane carrier 3, at which the detection zone 3y is to be provided. As the method for surface treatment, the aforementioned method can be used.

In the embodiment, as the detection substance (reagent), for example, an antibody is mentioned. The antibody is an antibody which binds to a target substance through an antigen-antibody reaction, and may be a polyclonal antibody or a monoclonal antibody.

The color change in the detection zone 3y may be produced by a label having an antibody or an antigen-binding fragment thereof specifically reacting with a target substance in a liquid sample. The color change is produced by, for example, holding a label by a detection substance (through a reaction with (binding to) the detection substance) in the detection zone 3y and producing a color.

The label is, for example, a label in which an antibody or an antigen-binding fragment thereof is bound to particles such as colloidal particles and latex particles. The antigen-binding fragment refers to a fragment specifically binding to a target substance, such as an antigen-binding fragment of an antibody. The label can bind to a target substance via an antibody or an antigen-binding fragment thereof. The particles may have magnetic property or fluorogenicity. Examples of the colloidal particles include metallic colloidal particles such as gold colloidal particles and platinum colloidal particles. The particles are preferably latex particles in view of control of particle size, dispersion stability and binding ability. The material for latex particles is not particularly limited; however, polystyrene is preferable.

In view of visibility, the particles are preferably colored particles or fluorescent particles and more preferably colored particles. The colored particles are satisfactory if the color thereof is detectable by the naked eye. The fluorescent particles are satisfactory if they contain a fluorescence substance. The particles may be colored latex particles or fluorescent latex particles. If the particles are colored latex particles, the color change mentioned above is suitably detected visually. If the particles are fluorescent latex particles, the color change mentioned above is suitably detected by fluorescence-intensity measurement.

In order for the label as mentioned above to successfully react with a target substance in a liquid sample to be delivered dropwise, the label is provided to at least a part of the test kit 18. The label may be provided, for example, to a member in the test kit 18 or may be provided to at least a part (upstream the detection zone 3$y$) of the flow path 2 of the membrane carrier 3. The label reacted with (bound to) a target substance is held by a detection substance (through reaction (binding) of the detection substance with the target substance) in the detection zone 3$y$. In this manner, a color change (color produced by a label) is produced in the detection zone 3$y$.

A method for testing a liquid sample according to one aspect of the embodiment is a test method using the test kit 18.

The method for testing a liquid sample using the test kit 18 may comprise a step of preparing a mixed liquid sample by mixing the liquid sample and a label specifically binding to a target substance in the liquid sample to mutually bind the target substance and the label; a step of delivering a drop of the mixed liquid sample to the drop zone 3$x$ provided in the membrane carrier 3; a step of transporting the mixed liquid sample from the drop zone 3$x$ to the detection zone 3$y$ through the microstructure 7; and a step of detecting a color change (color of label) in the detection zone 3$y$.

Alternatively, the above test method may comprise a step of delivering a drop of a liquid sample to the drop zone 3$x$ in the surface of the membrane carrier 3; a step of transporting the liquid sample from the drop zone 3$x$ to the detection zone 3$y$ through the microstructure 7 with the help of capillary action exerted by the microstructure 7 (convex portions 8) formed on the surface of the membrane carrier 3; and a step of binding a target substance in a liquid sample to the label via the antibody or an antigen-binding fragment thereof, further, binding the target substance to a reagent immobilized in the detection zone 3$y$ and detecting a color change in the detection zone 3$y$ (optically determining the presence or absence of color change).

In the step of mutually binding a target substance and a label in the above test method, a method for mixing a liquid sample and the label is not particularly limited. For example, a method of adding a liquid sample in a container containing the label or a method of mixing a liquid containing, for example, a label, and a liquid sample may be employed. Alternatively, a filter is inserted in a drip opening of a container containing, for example, a liquid sample, and a label may be immobilized in the filter.

EXAMPLES

The embodiments will be described by way of Examples and Comparative Examples; however, the embodiments are not limited by these Examples.

Example 1-1

<Preparation of Membrane Carrier>

Thermal imprint was applied to a polystyrene sheet (Denka styrene sheet manufactured by Denka Company Limited, film thickness 300 μm) to form a membrane carrier, in which the diameter of the bottom of a conical-shape convex portion (of a microstructure) 8 (hereinafter sometimes referred to as "diameter of a convex portion" or "diameter") was 10 μm and the height of the conical-shape convex portion (of a microstructure) (hereinafter sometimes referred to as "height") was 10 μm and the conical-shaped convex portions were arranged in a staggered manner at the nearest distance between mutual convex portions of 5 μm, as shown in FIG. 3, and which had a mean surface roughness of 0.102 μm. The mean surface roughness was adjusted to be a predetermined value by applying sand blasting to the surface of a mold. The mean surface roughness values shown in Tables 1 and 2 each shows the mean surface roughness of a microstructure mean surface roughness of convex portions). The mean surface roughness was determined by a surface roughness analysis 3D electron microscope (ERA-600, manufactured by Elionix Inc.) (see, FIG. 7). Three conical-shaped convex portions 8 were arbitrarily chosen, and a roughness profile along a linear line 20 passing through the vertex center (center point 19 of a convex portion) of the convex portion 8 as a midpoint and having a length (20$d$) of 10 μm was measured with respect to each of the three convex portions 8. The roughness profiles of three linear lines 20 were subjected to tilt correction and corrected as the profiles of flat planes. The values of the mean surface roughness (Ra) defined in JIS B0601 were individually obtained by calculation. The data on the three convex portions were averaged and regarded as an evaluation value.

<Preparation of Detection Zone (Detection Section)>

The microstructure of a membrane carrier produced as mentioned above was coated with a metal plate serving as a mask such that only the portion at a distance of 0.7 to 1.0 cm from the edge was to be irradiated with energy, and then, UV was applied. The metal plate was prepared such that an opening is provided to the portion corresponding to a 0.7-1.0 cm portion above to expose the membrane carrier. As a masking method, a method of placing the metal plate on the membrane carrier was employed. In this manner, the surface-treated membrane carrier 3 was obtained. In FIG. 8, the 0.7-1.0 cm portion corresponds to the detection zone 3$y$ (surface treated section); whereas the metal plate corresponds to the shield 14.

<Immobilization of Detection Substance>

To the portion that UV treatment was applied as mentioned above, an anti-type A influenza NP antibody suspension solution and an anti-type B influenza NP antibody suspension solution were applied in a line width of 1 mm (coating amounts were 3 μL) and sufficiently dried by hot air. In this manner, an anti-type A influenza NP antibody and an anti-type B influenza NP antibody were immobilized in the detection zone 3$y$.

<Preparation of Label>

A purified anti-type A influenza virus NP antibody (another antibody as used in the above) and a purified anti-type B influenza virus NP antibody (another antibody as used in the above) were used. The anti-type A influenza virus NP antibody was covalently labeled with red latex particles (CM/BL made from Ceradyne Inc.) having a particle size of 0.394 μm, suspended in a Tris buffer solution containing a sugar, a surfactant and a protein such that the concentration of the latex particles became 0.025 w/v %, and ultrasonically treated to prepare an anti-type A label sufficiently dispersed and suspended. Anti-type B label was similarly prepared by labeling an anti-type B influenza virus NP antibody with blue latex particles (CM/BL made from Ceradyne Inc.

The anti-type A label and the anti-type B label were mixed to prepare a mixed solution. The mixed solution was applied to the glass fiber having a size of 3 cm×1 cm (33GLASS No. 10539766, manufactured by Schleicher & Schuell) in an amount of 50 μL per square centimeter and dried well under hot air to produce a labeled pad. Thereafter, the labeled pad was overlapped with one of the edge portions of the membrane carrier (corresponding to the surface-treated membrane carrier 3) closer to the detection zone 13y. The width (width of the edge portion) of the membrane carrier overlapped with the labeled pad was 2 mm. The membrane carrier overlapped with the labeled pad was cut into strips having a width of 5 mm by a cutter to prepare liquid sample test kits integrally formed of the mere crane carrier and the labeled pad.

On the edge of the liquid sample test kit prepared as mentioned above, a liquid sample (100 μL) was added dropwise. The edge portion of the liquid sample test kit, on which the sample was added dropwise, was one of the edge portions closer to the detection zone. As the liquid sample, two types of samples were used; one is a type A influenza virus, A/Beijing/32/92 (H3N2) solution diluted with a specimen suspension solution attached to Quick navi-Flu manufactured by Denka Seiken Co., Ltd. as a dilution solution, up to $2 \times 10^4$ fold, and the other is a type B influenza virus B/Shangdong/7/97 solution diluted up to $2 \times 10^3$ fold.

Determination of detection was made by visually observing the presence or absence of a colored line (in the portion to which an anti-type A influenza NP antibody and an anti-type B influenza NP antibody were immobilized) in the detection zones (type A influenza virus detection section and type B influenza virus detection section) 15 minutes after dropwise addition of a liquid sample. Moving of the liquid sample added dropwise on the test kit was checked based on an average flow velocity and whether the liquid sample moved or not was confirmed. The average flow velocity was obtained by calculation based on the time from initiation of flow-out of the liquid sample added dropwise onto the edge portion of the liquid sample test kit until arrival of the liquid sample to the colored line of the detection zone.

As a result of determination, in the case of using the A/Beijing/32/92 (H3N2) dilution solution up to $2 \times 10^4$ fold, a color change was observed only in the type A detection zone; whereas in the case of using the B/Shangdong/7/97 dilution solution up to $2 \times 10^3$ fold, a color change was observed only in the type B detection zone.

Then, a maximum dilution rate at which the presence or absence of a colored line cannot be visually observed 15 minutes after initiation of the test was obtained by increasing the dilution rate of type A influenza virus A/Beijing/32/92 (H3N2) from $2 \times 10^4$ and regarded as the maximum visible-determination allowable dilution rate of type A. Subsequently, a maximum dilution rate at which the presence or absence of a colored line cannot be visually observed was obtained by increasing the dilution rate of type B influenza virus B/Shangdong/7/97 from $2 \times 10^3$ and regarded as the maximum visible-determination allowable dilution rate of type B.

Example 1-2

A liquid sample test kit was prepared in the same conditions as in Example 1-1 except that the diameter and the height of the conical-shape convex portion were set to 100 μm and 100 μm, respectively, and the mean surface roughness was set to 0.094 μm for the microstructure in Example 1-1.

Example 1-3

A liquid sample test kit was prepared in the same conditions as in Example 1-1 except that the diameter and the height of the conical-shape convex portion were set to 500 μm and 500 μm, respectively, and the mean surface roughness was set to 0.109 μm for the microstructures in Example 1-1.

Example 1-4

A liquid sample test kit was prepared in the same conditions as in Example 1-1 except that the diameter and the height of the conical-shape convex portion were set to 1000 μm and 100 μm, respectively, and the mean surface roughness was set to 0.121 μm for the microstructures in Example 1-1.

Example 1-5

A liquid sample test kit was prepared in the same conditions as in Example 1-1 except that the diameter and the height of the conical-shape convex portion were set to 100 μm and 10 μm, respectively, and the mean surface roughness was set to 0.094 μm for the microstructures in Example 1-1.

Example 1-6

A liquid sample test kit was prepared in the same conditions as in Example 1-1 except that the diameter and the height of the conical-shape convex portion were set to 100 μm and 200 μm, respectively, and the mean surface roughness was set to 0.120 μm for the microstructures in Example 1-1.

Example 1-7

A liquid sample test kit was prepared in the same conditions as in Example 1-1 except that the diameter and the height of the conical-shape convex portion were set to 100 μm and 100 μm, respectively, and the mean surface roughness was set to 0.048 μm for the microstructures in Example 1-1.

Example 1-8

A liquid sample test kit was prepared in the same conditions as in Example 1-1 except that the diameter and the height of the conical-shape convex portion were set to 100 μm and 100 μm, respectively, and the mean surface roughness was set to 0.015 μm for the microstructures in Example 1-1 were defined as conical-shaped convex portions having a diameter of 100 μm, a height of 100 μm and a mean surface roughness of 0.015 μm.

Example 1-9

A liquid sample test kit was prepared in the same conditions as in Example 1-1 except that the diameter and the height of the conical-shape convex portion were set to 100 µm and 100 µm, respectively, and the mean surface roughness was set to 0.27 µm for the microstructures in Example 1-1.

Example 1-10

A liquid sample test kit was prepared in the same conditions as in Example 1-1 except that the diameter and the height of the conical-shape convex portion were set to 100 µm and 100 µm, respectively, and the mean surface roughness was set to 6.8 µm for the microstructures in Example 1-1.

Example 1-11

A liquid sample test kit was prepared in the same conditions as in Example 1-1 except that the diameter and the height of the conical-shape convex portion were set to 100 µm and 100 µm, respectively; the nearest distance between microstructures was set to 100 µm, and the mean surface roughness was set to 0.095 µm for the microstructures in Example 1-1.

Example 1-12

A liquid sample test kit was prepared in the same conditions as in Example 1-1 except that the diameter and the height of the conical-shape convex portion were set to 100 µm and 100 µm, respectively, the nearest distance between microstructures was set to 500 µm, and the mean surface roughness was set to 0.058 µm for the microstructures in Example 1-1.

Comparative Example 1-1

A liquid sample test kit was prepared in the same conditions as in Example 1-1 except that the diameter and the height of the conical-shape convex portion were set to 100 µm and 100 µm, respectively, and the mean surface roughness was set to 0.002 µm for the microstructures in Example 1-1.

Comparative Example 1-2

A liquid sample test kit was prepared in the same conditions as in Example 1-1 except that the diameter and the height of the conical-shape convex portion were set to 100 µm and 100 µm, respectively, and the mean surface roughness was set to 17 µm for the microstructures in Example 1-1.

Evaluation results of the liquid sample test membrane carriers and liquid sample test kits obtained in Examples 1-1 to 1-12 and Comparative Examples 1-1 to 1-2 are shown in Table 1.

TABLE 1

| | Example 1-1 | Example 1-2 | Example 1-3 | Example 1-4 | Example 1-5 | Example 1-6 | Example 1-7 |
|---|---|---|---|---|---|---|---|
| Diameter of microstructure (convex portion) (µm) | 10 | 100 | 500 | 1000 | 100 | 100 | 100 |
| Nearest distance between microstructures (convex portions) (µm) | 5 | 5 | 5 | 5 | 5 | 5 | 5 |
| Height of microstructure (convex portion) (µm) | 10 | 100 | 500 | 100 | 10 | 200 | 100 |
| Aspect ratio | 1 | 1 | 1 | 0.1 | 0.1 | 2 | 1 |
| Average flow rate (mm/s) | 1.2 | 3.2 | 3.5 | 3.0 | 1.3 | 3.3 | 3.2 |
| Mean surface roughness (µm) | 0.102 | 0.094 | 0.109 | 0.121 | 0.094 | 0.120 | 0.048 |
| Maximum visible-determination allowable dilution rate of type A | $8 \times 10^4$ | $9 \times 10^4$ | $1 \times 10^5$ | $9 \times 10^4$ | $8 \times 10^4$ | $9 \times 10^4$ | $7 \times 10^4$ |
| Maximum visible-determination allowable dilution rate of type B | $8 \times 10^3$ | $9 \times 10^3$ | $1 \times 10^4$ | $9 \times 10^{103}$ | $8 \times 10^3$ | $9 \times 10^3$ | $7 \times 10^3$ |

| | Example 1-8 | Example 1-9 | Example 1-10 | Example 1-11 | Example 1-12 | Comparative Example 1-1 | Comparative Example 1-2 |
|---|---|---|---|---|---|---|---|
| Diameter of microstructure (convex portion) (µm) | 100 | 100 | 100 | 100 | 100 | 100 | 100 |
| Nearest distance between microstructures (convex portions) (µm) | 5 | 5 | 5 | 100 | 500 | 5 | 5 |

TABLE 1-continued

| | | | | | | | |
|---|---|---|---|---|---|---|---|
| Height of microstructure (convex portion) (μm) | 100 | 100 | 100 | 100 | 100 | 100 | 100 |
| Aspect ratio | 1 | 1 | 1 | 1 | 1 | 1 | 1 |
| Average flow rate (mm/s) | 3.2 | 3.2 | 3.2 | 0.33 | 0.15 | 3.2 | 3.2 |
| Mean surface roughness (μm) | 0.015 | 0.27 | 6.8 | 0.095 | 0.058 | 0.002 | 17 |
| Maximum visible-determination allowable dilution rate of type A | $5 \times 10^4$ | $9 \times 10^4$ | $4 \times 10^4$ | $8 \times 10^4$ | $7 \times 10^4$ | $1 \times 10^4$ | $1 \times 10^4$ |
| Maximum visible-determination allowable dilution rate of type B | $5 \times 10^3$ | $9 \times 10^4$ | $4 \times 10^3$ | $8 \times 10^3$ | $7 \times 10^3$ | $1 \times 10^3$ | $1 \times 10^3$ |

From the results of Table 1, it was shown that the liquid sample test kit according to the embodiment produces microcapillary flow by adjusting the height and diameter of microstructures in the flow path, the nearest distance between microstructures and the aspect ratio to fall appropriate ranges; and that a detection substance can be highly sensitively detected by adjusting a mean surface roughness of microstructures to fall within the proper range, thereby increasing the antibody amount immobilized in the detection zone.

Examples 1-13 to 1-24

The particles to be used were changed from colored latex particles to fluorescent latex particles (Micromer-F fluorescent latex particles, material: polystyrene, manufactured by Corefront Corporation). The dilution rate (maximum fluorescence determination allowable dilution rate) at which the presence or absence of a colored line cannot be read by an immunochromato reader (C11787 manufactured by Hamamatsu Photonics K. K.) 10 minutes after initiation of the test, in other words, the dilution rate at which the S/N ratio is 10 or less, was obtained. The diameter of microstructures, the nearest distance between microstructures and the height and aspect ratio of microstructures were shown in Table 2. The contents other than these were the same as in Examples 1-1 to 1-12.

Evaluation results of the membrane carriers for a liquid sample test kits and liquid sample test kits obtained in Examples 1-13 to 1-24 are shown in Table 2.

TABLE 2

| | Example 1-13 | Example 1-14 | Example 1-15 | Example 1-16 | Example 1-17 | Example 1-18 |
|---|---|---|---|---|---|---|
| Diameter of microstructure (convex portion) (μm) | 10 | 100 | 500 | 1000 | 100 | 100 |
| Nearest distance between microstructures (convex portions) (μm) | 5 | 5 | 5 | 5 | 5 | 5 |
| Height of microstructure (convex portion) (μm) | 10 | 100 | 500 | 100 | 10 | 200 |
| Aspect ratio | 1 | 1 | 1 | 0.1 | 0.1 | 2 |
| Average flow rate (mm/s) | 1.2 | 3.2 | 3.5 | 3.0 | 1.3 | 3.3 |
| Mean surface roughness (μM) | 0.102 | 0.094 | 0.109 | 0.121 | 0.094 | 0.120 |
| Maximum visible-determination allowable dilution rate of type A | $5 \times 10^6$ | $5 \times 10^6$ | $6 \times 10^6$ | $5 \times 10^6$ | $5 \times 10^6$ | $5 \times 10^6$ |
| Maximum visible-determination allowable dilution rate of type B | $5 \times 10^5$ | $5 \times 10^5$ | $6 \times 10^5$ | $5 \times 10^5$ | $5 \times 10^5$ | $5 \times 10^5$ |
| | Example 1-19 | Example 1-20 | Example 1-21 | Example 1-22 | Example 1-23 | Example 1-24 |
| Diameter of microstructure (convex portion) (μm) | 100 | 100 | 100 | 100 | 100 | 100 |

TABLE 2-continued

| | | | | | | |
|---|---|---|---|---|---|---|
| Nearest distance between microstructures (convex portions) (μm) | 5 | 5 | 5 | 5 | 100 | 500 |
| Height of microstructure (convex portion) (μm) | 100 | 100 | 100 | 100 | 100 | 100 |
| Aspect ratio | 1 | 1 | 1 | 1 | 1 | 1 |
| Average flow rate (mm/s) | 3.2 | 3.2 | 3.2 | 3.2 | 0.33 | 0.15 |
| Mean surface roughness (μM) | 0.048 | 0.015 | 0.27 | 6.8 | 0.095 | 0.058 |
| Maximum visible-determination allowable dilution rate of type A | $4 \times 10^6$ | $3 \times 10^6$ | $5 \times 10^6$ | $2 \times 10^6$ | $5 \times 10^6$ | $4 \times 10^6$ |
| Maximum visible-determination allowable dilution rate of type B | $4 \times 10^5$ | $3 \times 10^5$ | $5 \times 10^5$ | $2 \times 10^5$ | $5 \times 10^5$ | $4 \times 10^5$ |

In the embodiment, the amount of the detection substance to be immobilized can be increased by controlling a mean surface roughness of a membrane carrier surface, thereby improving detection sensitivity.

In the embodiment, in an immunochromatographic method, which enables optical confirmation that a target substance was detected, a mean surface roughness of a material is controlled to increase a signal of a detection zone. In this manner, a liquid sample test kit that enables highly sensitive determination is provided.

Example 2-1

<Preparation of Membrane Carrier>

Thermal imprint was applied to a polystyrene sheet (Denka styrene sheet manufactured by Denka Company Limited, film thickness 300 μm) to form a membrane carrier 3 in which convex portions 8 having a diameter of the bottom (hereinafter sometimes referred to as "diameter of a convex portion" or "diameter") of 10 μm and a height (hereinafter sometimes referred to as "height") of 10 μm were arranged in a staggered manner at the nearest distance between the microstructures of 5 μm, as shown in FIG. 3. The microstructure of a membrane carrier produced as mentioned above was masked with a metal plate such that only the portion at a distance of 0.7 to 1.0 cm from the edge can be irradiated with energy and then, UV was applied to prepare a membrane carrier having a ratio of number of oxygen atoms (number of oxygen atoms/(number of carbon atoms+number of nitrogen atoms+number of oxygen atoms)) of 0.35. The ratio of number of oxygen atoms was controlled by varying amount, intensity, wavelength and irradiation time of UV and energy of UV irradiation during the treatment with UV.

An opening was provided in the 0.7-1.0 cm portion of the metal plate to expose the membrane carrier. As a masking method, a method of placing the metal plate on the membrane carrier was employed. In this manner, the surface-treated membrane carrier 3 was obtained. In FIG. 8, the 0.7-1.0 cm portion corresponds to the detection zone 3y; whereas the metal plate corresponds to the shield 14.

<Calculation of Ratio of Number of Oxygen Atoms>

Half-quantity values of individual atoms were obtained by XPS. As a measuring device, K-ALPHA manufactured by Thermo SCIENTIFIC was used. The measurement conditions were as follows. As an X ray source, an Al—Kα ray (with a monochromator) was used; electric neutralization was carried out by dual beams, which was coaxial irradiation of i.e., a low speed electron and low speed Ar$^+$ ion; a detection angle was 90°, output: 36 W, measurement area: about 400 μm×200 μm, pass energy: 50 eV, data were taken in the conditions of 0.1 eV/step for 50 msec., and cumulated number: 5 times. The range of measurement was as follows: carbon C1s spectrum: 279 to 298 eV, oxygen O1s spectrum: 525 to 545 eV and nitrogen N1s spectrum: 392 to 410 eV. The binding-energy correction of the obtained spectrum was carried out based on the C—C bond (284.8 eV) in the C1s spectrum. With respect to the spectra after the binding energy correction was carried out, correction was made in the following range by subtracting background (BG) in accordance with the Shirley method, as follows. Carbon C1s spectrum: 281 to 292 eV, oxygen O1s spectrum: 526 to 536 eV and nitrogen N1s spectrum: 395 to 403 eV. The peak areas (signal intensity) of individual atoms obtained by subtracting BG from the respective peaks obtained in the above measurement ranges were divided by the correction coefficients (relative sensitivity coefficient, transparent function, kinetic energy correction) and calculation was made such that the total of the areas after correction became 100. The individual values thus obtained were regarded as the number of carbon atoms, the number of nitrogen atoms, and the number of oxygen atoms, and the ratio of number of oxygen atoms (number of oxygen atoms/(number of carbon atoms+number of nitrogen atoms+number of oxygen atoms)) was calculated.

<Immobilization of Detection Substance>

To a surface-treated portion of a membrane carrier (corresponding to detection zone 3y), a suspension of an anti-type A influenza NP antibody and a suspension of an anti-type B influenza NP antibody were applied in a line width of 1 mm (coating amount 3 μL), and dried well under hot air. In this manner, the anti-type A influenza NP antibody and the anti-type B influenza NP antibody were immobilized in the detection zone 3y.

<Immobilization of Label>

A purified anti A influenza virus NP antibody (another antibody as used in the above) and a purified anti B influenza virus NP antibody (another antibody as used in the above) were used. The anti-type A influenza NP antibody was covalently labeled with red latex particles having a particle size of 0.394 µm (CM/BL, manufactured by Ceradyne Inc.), suspended in a Tris buffer solution containing a sugar, a surfactant and a protein such that the concentration of the latex particles became 0.025 w/v %, and ultrasonically treated to prepare an anti-type A label sufficiently dispersed and suspended. Similarly, the anti-type B influenza virus NP antibody was labeled with blue latex particles (CM/BL, manufactured by Ceradyne Inc.) to prepare anti-type B label.

The anti-type A label and the anti-type B label were mixed to prepare a mixture. The mixture was applied to the glass fiber having a size of 3 cm×1 cm (33GLASS No. 10539766, manufactured by Schleicher & Schuell) in an amount of 50 µL per square centimeter and dried well under hot air to give a labeled pad. Thereafter, the labeled pad was overlapped with one of the edge portions of the membrane carrier (corresponding to a surface-treated membrane carrier 3) prepared as mentioned above, and closer to the detection zone 13$y$. The width (width of the edge portion) of the membrane carrier overlapped with the labeled pad was 2 mm. The membrane carrier overlapped with the labeled pad was cut into strips having a width of 5 mm by a cutter to prepare liquid sample test kits integrally formed of the membrane carrier and the labeled pad.

On the edge of the liquid sample test kit prepared as mentioned above, the liquid sample (100 µL) was added dropwise. The edge of the liquid sample test kit at which the liquid sample was added dropwise was one of the edge portions closer to the detection zone. Two types of liquid samples were prepared as follows. As a detection substance, type A influenza virus A/Beijing/32/92(H3N2) and type B influenza virus B/Shangdong/7/97, were used. As a dilution solution, a specimen suspension solution attached to Quick Navigation-Flu, manufactured by Denka Seiken Co., Ltd., was used. Type A influenza virus A/Beijing/32/92(H3N2) was diluted with the specimen suspension solution up to $2 \times 10^4$ fold and used as liquid sample A. Type B influenza virus B/Shangdong/7/97 was diluted with the specimen suspension solution tip to $2 \times 10^3$ fold and used as liquid sample B. Liquid sample A and liquid sample B were separately added dropwise.

Determination of detection was made by visually observing the presence or absence of a colored line (in the portions at which the anti-type A influenza NP antibody and the anti-type B influenza NP antibody were immobilized) in the detection zones (an type A influenza virus detection section and type-B influenza virus detection section), 15 minutes after dropwise addition of a liquid sample. Whether the liquid sample moved or not was checked by visually observing movement of the liquid sample added dropwise on the test kit.

As a result of determination, in the case of using the A/Beijing/32/92 (H3N2) dilution solution up to $2 \times 10^4$ fold, a color change was observed only in the type A detection zone; whereas in the case of using the B/Shangdong/7/97 dilution solution up to $2 \times 10^3$ fold, a color change was observed only in the type B detection zone.

Then, a maximum dilution rate at which the presence or absence of a colored line cannot be visually observed 15 minutes after initiation of the test was obtained by increasing the dilution rate of type A influenza virus A/Beijing/32/92 (H3N2) from $2 \times 10^4$. Subsequently, a maximum dilution rate at which the presence or absence of a colored line cannot be visually observed was obtained by increasing the dilution rate of type B influenza virus B/Shangdong/7/97 from $2 \times 10^3$.

Example 2-2

A liquid sample test kit was prepared in the same conditions as in Example 2-1 except that the diameter and the height of the conical-shaped convex portion were set to 100 µm and 100 µm, respectively, for the microstructures of Example 2-1.

Example 2-3

A liquid sample test kit was prepared in the same conditions as in Example 2-1 except that the diameter and the height of the conical-shaped convex portion were set to 500 µm and 500 µm, respectively, for the microstructures of Example 2-1.

Example 2-4

A liquid sample test kit was prepared in the same conditions as in Example 2-1 except that the diameter and the height of the conical-shaped convex portion were set to 1000 µm and 100 µm, respectively, for the microstructures of Example 2-1.

Example 2-5

A liquid sample test kit was prepared in the same conditions as in Example 2-1 except that the diameter and the height of the conical-shaped convex portion were set to 100 µm and 10 µm, respectively, for the microstructures of Example 2-1.

Example 2-6

A liquid sample test kit was prepared in the same conditions as in Example 2-1 except that the diameter and the height of the conical-shaped convex portion were set to 100 µm and 200 µm, respectively, for the microstructures of Example 2-1.

Example 2-7

A liquid sample test kit was prepared in the same conditions as in Example 2-1 except that the diameter and the height of the conical-shaped convex portion were set to 100 µm and 100 µm, respectively, and the ratio of number of oxygen atoms was set to 0.12 for the microstructures of Example 2-1.

Example 2-8

A liquid sample test kit was prepared in the same conditions as in Example 2-1 except that the diameter and the height of the conical-shaped convex portion were set to 100 µm and 100 µm, respectively, and the ratio of number of oxygen atoms was set to 0.05 for the microstructures of Example 2-1.

Example 2-9

A liquid sample test kit was prepared in the same conditions as in Example 2-1 except that the microstructures of Example 2-1 were defined as conical-shaped convex portions having a diameter of 100 µm and a height of 100 µm; and the ratio of number of oxygen atoms was set to be 0.01.

Example 2-10

A liquid sample test kit was prepared in the same conditions as in Example 2-1 except that the diameter and the height of the conical-shaped convex portion were set to 100

µm and 100 µm, respectively, and the nearest distance between microstructures was set to be 100 µm for the microstructures of Example 2-1.

Example 2-11

A liquid sample test kit was prepared in the same conditions as in Example 2-1 except that the diameter and the height of the conical-shaped convex portion were set to 100 µm and 100 µm, respectively, and the nearest distance between microstructures was set to be 500 µm for the microstructures of Example 2-1.

Example 2-12

A liquid sample test kit was prepared in the same conditions as in Example 2-1 except that the diameter and the height of the conical-shaped convex portion were set to 100 µm and 100 µm, respectively; and the ratio of number of oxygen atoms was set to 0.50 for the microstructures of Example 2-1.

Comparative Example 2-1

A liquid sample test kit was prepared in the same conditions as in Example 2-1 except that the diameter and the height of the conical-shaped convex portion were set to 100 µm and 100 µm, respectively; no UV irradiation was applied; and the ratio of number of oxygen atoms was set to 0.005 for the microstructures of Example 2-1.

Evaluation results of the liquid sample test membrane carrier and liquid sample test kits obtained in Examples 2-1 to 2-12 and Comparative Example 2-1 are shown in Table 3.

TABLE 3

|  | Example 2-1 | Example 2-2 | Example 2-3 | Example 2-4 | Example 2-5 | Example 2-6 | Example 2-7 |
|---|---|---|---|---|---|---|---|
| Diameter of microstructure (convex portion) (µm) | 10 | 100 | 500 | 1000 | 100 | 100 | 100 |
| Nearest distance between microstructures (convex portions) (µm) | 5 | 5 | 5 | 5 | 5 | 5 | 5 |
| Height of microstructure convex portion) (µm) | 10 | 100 | 500 | 100 | 10 | 200 | 100 |
| Aspect ratio | 1 | 1 | 1 | 0.5 | 0.5 | 2 | 1 |
| Ratio of number of oxygen atoms | 0.35 | 0.35 | 0.35 | 0.35 | 0.35 | 0.35 | 0.12 |
| Maximum visible-determination allowable dilution rate of type A | $7 \times 10^4$ | $8 \times 10^4$ | $9 \times 10^4$ | $8 \times 10^4$ | $7 \times 10^4$ | $8 \times 10^4$ | $6 \times 10^4$ |
| Maximum visible-determination allowable dilution rate of type B | $7 \times 10^3$ | $8 \times 10^3$ | $9 \times 10^4$ | $8 \times 10^3$ | $7 \times 10^3$ | $8 \times 10^3$ | $6 \times 10^3$ |

|  | Example 2-8 | Example 2-9 | Example 2-10 | Example 2-11 | Example 2-12 | Comparative Example 2-1 |
|---|---|---|---|---|---|---|
| Diameter of microstructure (convex portion) (µm) | 100 | 100 | 100 | 100 | 100 | 100 |
| Nearest distance between microstructures (convex portions) (µm) | 5 | 5 | 100 | 500 | 5 | 5 |
| Height of microstructure convex portion) (µm) | 100 | 100 | 100 | 100 | 100 | 100 |
| Aspect ratio | 1 | 1 | 1 | 1 | 1 | 1 |
| Ratio of number of oxygen atoms | 0.05 | 0.01 | 0.35 | 0.35 | 0.50 | 0.005 |
| Maximum visible-determination allowable dilution rate of type A | $5 \times 10^4$ | $4 \times 10^4$ | $7 \times 10^4$ | $6 \times 10^4$ | $1 \times 10^5$ | $1 \times 10^4$ |
| Maximum visible-determination allowable dilution rate of type B | $5 \times 10^3$ | $4 \times 10^4$ | $7 \times 10^3$ | $6 \times 10^3$ | $1 \times 10^4$ | $1 \times 10^3$ |

Comparative Example 2-2

A liquid sample test kit was prepared in the same conditions as in Example 2-1 except that the diameter and the height of the conical-shaped convex portion were set to 100 µm and 100 µm, respectively and the ratio of number of oxygen atoms was set to 0.50 for the microstructures of Example 2-1.

The evaluation results of liquid sample detection membrane carrier obtained in Comparative Example 2-2 are shown in Table 4. As a liquid sample, a liquid sample containing no viruses was used. The same procedure was repeated with respect to Example 2-2 and Example 2-12.

TABLE 4

|  | Example 2-2 | Example 2-12 | Comparative Example 2-2 |
|---|---|---|---|
| Diameter of microstructure (convex portion) (μm) | 100 | 100 | 100 |
| Nearest distance between microstructures (convex portions) (μm) | 5 | 5 | 5 |
| Height of microstructure (convex portion) (μm) | 100 | 100 | 100 |
| Aspect ratio | 1 | 1 | 1 |
| Ratio of number of oxygen atoms | 0.35 | 0.50 | 0.55 |
| Evaluation results when a liquid sample containing no viruses were developed | Staining was not observed | Staining was slightly observed | Staining was apparently observed when a liquid sample containing no viruses was developed. |

From the results of Tables 3 and 4, it was demonstrated that the liquid sample test kit according to the embodiment produces capillary flow. In the embodiment, it was demonstrated that a detection substance can be highly sensitively detected with a low possibility of a false detection by controlling an ratio of number of oxygen atoms to fall within an appropriate range (for example, see Example 2-2, Examples 2-7 to 2-9 and Example 2-12). In the embodiment, it was demonstrated that a detection substance can be highly sensitively detected by adjusting the height of microstructures in the flow path to fall within the proper range (for example, see Example 2-2 and Example 2-4). If the ratio of number of oxygen atoms is low, highly sensitive determination was not be made (Comparative Example 2-1); whereas if the ratio of number of oxygen atoms is high, false detection occurred (Comparative Example 2-2).

Examples 2-13 to 2-24

The particles to be used were changed from colored latex particles to fluorescent latex particles (Micromer-F fluorescent latex particles, material: polystyrene, manufactured by Corefront Corporation). The dilution rate (maximum fluorescence determination allowable dilution rate) at which the presence or absence of a colored line cannot be read by an immunochromato reader (C11787 manufactured by Hamamatsu Photonics K. K.) 10 minutes after initiation of the test, in other words, the dilution rate at which the S/N ratio is 10 or less, was obtained. The diameter of microstructures, the nearest distance between microstructures and height of microstructures and aspect ratio were shown in Table 5. The contents other than these were the same as in Examples 2-1 to 2-12.

The evaluation results of membrane carriers for a liquid sample test kit and liquid sample test kits obtained in Examples 2-13 to 2-24 are shown in Table 5.

TABLE 5

|  | Example 2-13 | Example 2-14 | Example 2-15 | Example 2-16 | Example 2-17 | Example 2-18 |
|---|---|---|---|---|---|---|
| Diameter of microstructure (convex portion) (μm) | 10 | 100 | 500 | 1000 | 100 | 100 |
| Nearest distance between microstructures (convex portions) (μm) | 5 | 5 | 5 | 5 | 5 | 5 |
| Height of microstructure (convex portion) (μ) | 10 | 100 | 500 | 100 | 10 | 200 |
| Aspect ratio | 1 | 1 | 1 | 0.5 | 0.5 | 2 |
| Ratio of number of oxygen atoms | 0.35 | 0.35 | 0.35 | 0.35 | 0.35 | 0.35 |
| Maximum visible-determination allowable dilution rate of type A | $4 \times 10^6$ | $5 \times 10^6$ | $5 \times 10^6$ | $5 \times 10^6$ | $4 \times 10^6$ | $5 \times 10^6$ |
| Maximum visible-determination allowable dilution rate of type B | $4 \times 10^5$ | $5 \times 10^5$ | $5 \times 10^5$ | $5 \times 10^5$ | $4 \times 10^5$ | $5 \times 10^5$ |

|  | Example 2-19 | Example 2-20 | Example 2-21 | Example 2-22 | Example 2-23 | Example 2-24 |
|---|---|---|---|---|---|---|
| Diameter of microstructure (convex portion) (μm) | 100 | 100 | 100 | 100 | 100 | 100 |
| Nearest distance between microstructures (convex portions) (μm) | 5 | 5 | 5 | 100 | 500 | 5 |
| Height of microstructure (convex portion) (μ) | 100 | 100 | 100 | 100 | 100 | 100 |
| Aspect ratio | 1 | 1 | 1 | 1 | 1 | 1 |
| Ratio of number of oxygen atoms | 0.12 | 0.05 | 0.01 | 0.35 | 0.35 | 0.50 |
| Maximum visible-determination allowable dilution rate of type A | $4 \times 10^6$ | $3 \times 10^6$ | $2 \times 10^6$ | $4 \times 10^6$ | $4 \times 10^6$ | $6 \times 10^6$ |

TABLE 5-continued

| | | | | | | |
|---|---|---|---|---|---|---|
| Maximum visible-determination allowable dilution rate of type B | $4 \times 10^5$ | $3 \times 10^5$ | $2 \times 10^5$ | $4 \times 10^5$ | $4 \times 10^5$ | $6 \times 10^5$ |

In the embodiment, in an immunochromatographic method which enables visual confirmation that a target substance was detected the number of oxygen atoms in a detection zone is controlled to increase the intensity of a signal in the detection zone. In this manner, a liquid sample test kit that enables highly sensitive determination is provided.

Since the membrane carrier for a test kit is mass-produced in a short time, the ratio of number of oxygen atoms in the surface tended to be high and thus an amount of surface treatment applied to a material was relatively high. The embodiment where, for example, an ratio of number of oxygen atoms is specified, has an effect: the possibility of reacting a label with a detection substance when a solution containing no target substance is developed is low, in other words, the possibility of a wrong detection is low. For example, in the embodiment where the ratio of number of oxygen atoms in the surface of a detection zone is increased, thereby increasing an amount of an antibody to be immobilized to the detection zone, a detection substance can be highly sensitively detected.

The liquid sample test kit according to the embodiment enables implementation of a highly sensible test in a short time and is thus useful as a disposable POCT reagent.

REFERENCE SIGNS LIST

2: Flow path, 3: Membrane carrier having microstructures provided therein, 3x: Drop zone, 3y: Detection zone (Detection section), 4,4a,4b,4c,4d: Representative length of the bottom surface of a convex portion (diameter of convex-portion bottom), 5: Nearest distance between microstructures, 6,6a,6b,6c,6d: Height of convex portions, 7,7a,7b,7c,7d: Microstructure, 8,8a,8b,8c,8d: Convex portion, 9: Flat part, 10,10a,10b,10c,10d: Bottom surface of convex portions, Shield 14, 18: Test kit for liquid sample, 18a: Case, 18b: First opening, 18c: Second opening, 19: Center of convex portion, 20: Linear line passing through center of convex portion, 20d: Length of linear line passing through center of convex portion, d: Liquid sample flow direction (transport direction)

The invention claimed is:

1. A membrane carrier comprising a detection zone able to detect a target substance in the liquid sample, and a flow path able to transport the liquid sample;
   wherein a microstructure is formed at a bottom of the flow path, wherein the microstructure comprises a flat part along the bottom of the flow path and a plurality of convex portions that extend perpendicularly upward in a three-dimensional manner from the flat part along the bottom of the flow path,
   wherein multiple convex portions are disposed at the bottom of the flow path along a width and along a length of the flow path,
   wherein each of the plurality of convex portions has a height of 5 µm to 1000 µm and a bottom diameter of 10 µm to 500 µm,
   wherein a mean surface roughness (Ra) of the surface of the convex portions of the microstructure is 0.005 µm to 1.0 µm, wherein the convex portions are configured to produce capillary action in the microstructure of the flow path, and wherein the surface roughness of the convex portions is configured to increase an amount of a detection substance immobilized in the detection zone.

2. The membrane carrier according to claim 1, wherein a nearest distance between convex portions the microstructures in the flow path is 2 µm to 500 µm.

3. The membrane carrier according to claim 1, wherein an aspect ratio each of the plurality of convex portions in of the microstructure is 0.1 to 10.

4. The membrane carrier according to claim 1, being a membrane carrier for a detection kit, which detects a target substance in a liquid sample.

5. The membrane carrier according to claim 4, wherein the detection zone produces a color change when the target substance is detected.

6. The membrane carrier according to claim 4, wherein the detection substance produces the color change when the target substance is immobilized in the detection zone with the detection substance.

7. A liquid sample test kit having the membrane carrier according to claim 1.

8. The membrane carrier according to claim 1, wherein the convex portions have a height of 10 µm to 500 µm.

9. The membrane carrier according to claim 1, wherein an oxygen atom and at least one of a carbon atom and a nitrogen atom present on a surface of the detection zone, wherein a ratio of the number of oxygen atoms relative to a total number of individual types of atoms (number of oxygen atoms/(number of carbon atoms+number of nitrogen atoms+number of oxygen atoms)) is 0.01 to 0.30.

* * * * *